(12) United States Patent
Horak

(10) Patent No.: US 10,788,503 B2
(45) Date of Patent: Sep. 29, 2020

(54) METHODS AND APPARATUS FOR BEAD MANIPULATION IN A TIP OF A LIQUID HANDLER

(71) Applicant: Andrew Alliance S.A., Vernier (CH)

(72) Inventor: Giorgio Horak, Geneva (CH)

(73) Assignee: Andrew Alliance S.A., Vernier (CH)

( * ) Notice: Subject to any disclaimer, the term of this patent is extended or adjusted under 35 U.S.C. 154(b) by 356 days.

(21) Appl. No.: 15/463,432

(22) Filed: Mar. 20, 2017

(65) Prior Publication Data
US 2017/0269110 A1  Sep. 21, 2017

Related U.S. Application Data

(60) Provisional application No. 62/351,512, filed on Jun. 17, 2016, provisional application No. 62/310,084, filed on Mar. 18, 2016.

(51) Int. Cl.
*G01N 35/00* (2006.01)
*B01L 3/02* (2006.01)
(Continued)

(52) U.S. Cl.
CPC ........ *G01N 35/0098* (2013.01); *B01L 3/0275* (2013.01); *B03C 1/01* (2013.01);
(Continued)

(58) Field of Classification Search
CPC ............ G01N 35/0098; G01N 35/10; G01N 2035/1053; G01N 1/40; G01N 1/4077; G01N 2001/4038; B03C 1/288; B03C 1/30; B03C 1/0332; B03C 1/0335; B03C 1/01; B03C 1/032; B03C 1/286; B03C 2201/26; B03C 2201/18; B03C 2201/22; B03C 1/00; B03C 1/02; B03C 1/025; B01L 3/0275; B01L 2400/043; B01L 2200/0668;
(Continued)

(56) References Cited

U.S. PATENT DOCUMENTS

| 5,647,994 A * | 7/1997 | Tuunanen | ............... B03C 1/288 |
| | | | 210/695 |
| 5,942,124 A * | 8/1999 | Tuunanen | ........ G01N 33/54326 |
| | | | 210/695 |

(Continued)

FOREIGN PATENT DOCUMENTS

| CN | 101268189 A | 9/2008 |
| CN | 106102898 A | 11/2016 |

(Continued)

OTHER PUBLICATIONS

The International Preliminary Report on Patentability, Chapter I for PCT/IB2017/000326, dated Sep. 18, 2018. (Year: 2018).*

(Continued)

*Primary Examiner* — Joseph W Drodge
(74) *Attorney, Agent, or Firm* — Schmeiser, Olsen & Watts LLP

(57) ABSTRACT

The present invention is directed towards an apparatus and methods for a precise, fast and easy to use manipulation of beads. This method is particularly useful to carry out separation between the beads and the remaining supernants present in the fluid, maximizing the collection and purification efficiencies in tips for liquid handling.

14 Claims, 15 Drawing Sheets

(51) Int. Cl.

| | | |
|---|---|---|
| *B03C 1/28* | (2006.01) | |
| *B03C 1/30* | (2006.01) | |
| *B03C 1/01* | (2006.01) | |
| *B03C 1/03* | (2006.01) | |
| *C12N 15/10* | (2006.01) | |
| *G01N 35/10* | (2006.01) | |
| *B03C 1/032* | (2006.01) | |
| *B03C 1/033* | (2006.01) | |

(52) U.S. Cl.
CPC ............ *B03C 1/032* (2013.01); *B03C 1/0332* (2013.01); *B03C 1/0335* (2013.01); *B03C 1/286* (2013.01); *B03C 1/288* (2013.01); *B03C 1/30* (2013.01); *C12N 15/1013* (2013.01); *G01N 35/10* (2013.01); *B01L 2200/025* (2013.01); *B01L 2200/0647* (2013.01); *B01L 2200/0668* (2013.01); *B01L 2400/043* (2013.01); *B03C 2201/18* (2013.01); *B03C 2201/22* (2013.01); *B03C 2201/26* (2013.01); *G01N 2035/1053* (2013.01)

(58) Field of Classification Search
CPC ....... B01L 2200/0647; B01L 2200/025; B01L 3/02; B01L 2200/0652; B01L 2200/0688; C12N 15/1013; B01D 17/00
USPC .......... 422/524, 525; 436/177; 210/222, 695
See application file for complete search history.

(56) References Cited

U.S. PATENT DOCUMENTS

| | | | |
|---|---|---|---|
| 6,187,270 B1 | 2/2001 | Schmitt et al. | |
| 8,574,515 B2 * | 11/2013 | Ellis | ......... B03C 1/288 422/527 |
| 2002/0028926 A1 | 3/2002 | Shoji et al. | |
| 2003/0146166 A1 * | 8/2003 | Ras | ......... B03C 1/035 210/695 |
| 2004/0197780 A1 | 10/2004 | McKernan et al. | |
| 2008/0170966 A1 * | 7/2008 | Cook | ......... B03C 1/286 422/400 |
| 2008/0296157 A1 * | 12/2008 | Bauer | ......... B03C 1/288 204/557 |
| 2010/0285606 A1 * | 11/2010 | Phillips | ......... B01L 3/502761 436/501 |
| 2012/0196774 A1 * | 8/2012 | Fournier | ......... G01N 35/1065 506/32 |
| 2013/0273552 A1 | 10/2013 | Ohashi | |
| 2013/0288259 A1 * | 10/2013 | Tajima | ......... B01L 3/0217 435/6.12 |
| 2014/0248679 A1 * | 9/2014 | Zhang | ......... C12N 13/00 435/173.9 |
| 2015/0090664 A1 * | 4/2015 | Nokleby | ......... B01L 9/06 210/695 |
| 2015/0118688 A1 * | 4/2015 | Weidemaier | ......... C12M 23/08 435/7.1 |
| 2015/0135829 A1 * | 5/2015 | Whitesides | ......... G01B 21/00 73/32 R |
| 2017/0073667 A1 | 3/2017 | Ohashi et al. | |

FOREIGN PATENT DOCUMENTS

| | | | |
|---|---|---|---|
| EP | 0358948 A2 | 3/1990 | |
| EP | 0589636 A1 | 3/1994 | |
| EP | 0737110 A1 | 10/1996 | |
| EP | 0737110 B1 | 9/1999 | |
| EP | 0965842 A1 | 12/1999 | |
| EP | 1621890 A1 | 2/2006 | |
| JP | H02161358 A | 6/1990 | |
| JP | H06198214 A | 7/1994 | |
| JP | H0829424 A | 2/1996 | |
| JP | H0852378 A | 2/1996 | |
| JP | H08511721 A | 12/1996 | |
| JP | H11187862 A | 7/1999 | |
| JP | 2002085060 A | 3/2002 | |
| JP | 2003254877 A | 9/2003 | |
| JP | 3682302 B2 | 8/2005 | |
| JP | 2036635 A1 | 3/2009 | |
| JP | 2009508496 A | 3/2009 | |
| JP | 2009544975 A | 12/2009 | |
| WO | 2008014223 A2 | 1/2008 | |
| WO | 2009111769 A2 | 9/2009 | |
| WO | 2007148734 A1 | 11/2009 | |
| WO | 2015136689 A1 | 9/2015 | |
| WO | WO-2017158425 A1 * | 9/2017 | ......... B03C 1/01 |

OTHER PUBLICATIONS

Office Action in European Patent Application No. 17718988.3 dated Sep. 24, 2019.
International Preliminary Report on Patentability in PCT/IB2017/000326 dated Sep. 18, 2018.
International Search Report and Written Opinion in PCT/IB2017/000326 dated Aug. 7, 2017.
Office Action in European Patent Application No. 17718988.3 dated Mar. 9, 2020.

* cited by examiner

FIGS. 3A-B

METHODS AND APPARATUS FOR BEAD MANIPULATION IN A TIP OF A LIQUID HANDLER

FIELD OF THE INVENTION

The present invention relates to the field of automation of chemical, biological and biochemical process or reaction. More specifically, it discloses device and methods for separation of magnetic and non-magnetic particles in tips or orifices of liquid handling systems.

BACKGROUND OF THE INVENTION

The use of micro and nano-particles are of great interest for many technological applications: bio-sensing applications, medical and biological applications, such as modified drug delivery during medical treatment, bio-separation, purification and screening of antibodies and proteins, etc.

In general, we define as "bead" any tag, barcode, molecular beacon, sponge or particle from few Angstroms to several millimeters, capable to selectively transport one or more specific components under the influence of an external force.

In particular, magnetic separation technology has become a fundamental part of in DNA sequencing. In fact, magnetic separation technique not only is a relatively cheap and highly scalable methods, but offers many advantage with respect to similar methods, such as subjecting the sample to very little mechanical stress, high recovery efficiency and purification of the sample.

Magnetic beads are used as a carriers of proteins, cell, antibodies, antigens and nucleic acids by means of a suitable coating on the external surface of the particle. In fact, in order to be able to bind and capture the desired target analyte, the magnetic beads have to be coated with a ligand that specifically binds the target. The choice of the type of ligand will entirely depend on the target molecule that has to be captured.

The central core of the beads is magnetic and it is responsible of the ability to respond to an external magnetic field. Metal oxides are typically preferred because they are more stable to oxidation with respect to pure metals. The beads may possess single domain or multi-domain structure according to the size of the magnetic core. The size of beads mainly affects the coercivity: the smaller the beads are, the smaller is the coercivity. In particular, nanoparticles of the order of 5-15 nm are super-paragmatic, whereas microparticles are ferromagnetic.

The magnetic and physical properties of the beads are chosen according to the applications which the magnetic particles must be used for. Nanoparticles have the advantage of not having remanence, when the magnetic field is removed; at the same time, the magnetic force is so small that the viscous forces dominates: this implies a more difficult separation and movement of the particles.

In general, magnetic separation may be carried out with beads which show very weak integration with the poles of a magnet (paramagnetism), beads having high susceptibility to magnetization (ferromagnetism), beads which tend to become magnetized in a direction at 180° to the applied magnetic field (diamagnetism) or with ferromagnetic nanoparticles which shows superparamagnetism behavior.

In the magnetic bead separation, the first step is the binding of the sample to external coating of the beads. The liquid solution containing the target analyte is dispensed into a magnetic beads buffer. Typically, liquid mixing is carried out in order to increase the efficiency of the binding between the magnetic beads and the analyte.

The separation of the analyte is achieved by moving the beads by applied an external magnetic field, which will generate a force according to the following formula $$\vec{F} = \nabla(\vec{m} \cdot \vec{B})$$

A closer look at the formula shows that the magnetic force depends on the gradient of the magnetic field $\vec{B}$ and on the magnetic moment of the beads $\vec{B}$.

When the magnetic field is applied, the magnetic beads become magnetized and start forming clusters, which moves along the magnetic field gradient direction. After a certain amount of time which depends on the quantity and dimension of the beads, intensity of the magnetic field gradient and viscosity of the solution liquid, the magnetic beads are pelleted in a defined region which depends on the line of the magnetic field.

At this point, the sample separation is achieved by isolating the beads from the remaining liquid solution. Typically, either the remaining liquid solution is evacuated or the magnetic bead cluster is moved into another vessel.

Successively, the magnetic beads are immersed in a solution intended to detach the analytes from the magnetic beads. To optimize the collection of the samples from the beads, it may be required to re-suspend the beads, which implies to overcome the separation force between magnetic beads. In the end, the magnetic beads are separated once again in order to collect the supernants which contains, in this case, the target analytes.

The efficiency of the magnetic bead separation mainly depends on the quantity of the starting sample collected at the end of the process (collection efficiency), and the presence of unwanted substance which should have been removed during the separation technique (purification efficiency).

SUMMARY OF THE INVENTION

The present invention is directed towards an apparatus and methods for a precise, fast and easy to use manipulation of beads. This method is particularly useful to carry out separation between the beads and the remaining supernants present in the fluid, maximizing the collection and purification efficiencies in tips for liquid handling.

A tip for liquid handling is generally intended as removable or permanent interface between the fluid and the liquid handling system ("liquid handler" or "pipette"). In a specific implementation, the tip can be meant to contain the fluid aspirated and dispensed by the liquid handler. In the present disclosure, tips include among others microplates, tubes, needles, syringes, vacutainers, filters, containers, capillaries, and fluidic channels typically used in the field of liquid handling and biological or chemical reactions. Tips can be considered as disposable tips when they are used a single time (normally to prevent contamination) and when they can be reused multiple times (permanent tips).

A liquid handler is a manual accessory or automatic system capable to dispense a selected quantity of reagent, sample or other fluid. A liquid handler includes among others manual pipettes, syringes, pumps, valves, workstations, capillaries, micro-fluidic channels and liquid dispensers typically used in the field of liquid handling and biological or chemical reactions.

Within liquid handlers, we include devices capable of aspirating and dispensing a sample (also called pipettors)

and devices dispensing a certain aliquot of fluid from a reservoir at defined amounts (also called dispensers). We hereby disclose a specific class of liquid handlers intermediate between a pipettor and a dispenser, called dispenser, capable of switching their working modality between a pipettor and a dispenser, from collecting a sample in the tip to flushing one or more fluids through the same tip.

We define separation as a process that acting on the beads may disperse them homogeneously into a fluid, or aggregate the beads in a particular location, within or outside the fluid.

Accordingly, in one aspect of the present invention, a method is provided for separating the beads within a tip of a liquid hander. The method comprises a source of electrostatic, electrodynamic, electromagnetic, acoustic, mechanical, gravitational, nuclear, magnetic or thermal capable to apply a force to the beads which causes their separation. Once the beads cluster is formed, the separation is achieved by evacuation only the remaining fluid from the tip.

In yet another aspect of the present invention, an external force is applied to the bead cluster in order to keep it inside the tip during the evacuation of the fluid from the tip itself.

In yet another aspect of the present invention, the tip is designed in order to avoid the bead cluster to leave the tip during the evacuation of the fluid.

In yet another aspect of the present invention, once the beads are pelleted, the fluid is evacuated at a controlled flow rate in order to avoid generation of fluid-dynamic turbulences whose shearing forces are bigger than the cohesion forces of the bead cluster.

In yet another aspect of the present invention, the beads are moved by an action of the liquid hander and the external force, either simultaneous, sequential, independent or coordinates that allows to separate the beads form the fluid. The separation may occur within a container connected to a liquid handler or a generic aspiration or dispensing device. The connection may be permanent or removable and it can be achieved by mechanical contact or contactless by means of any external forces such as electromagnetic, acoustic, thermal, gravitational or magnetic.

In yet another aspect of the present invention, the bead containing sample is aspirated within the tip of a dispenser, then separated, and the switch to the dispenser mode of the dispenser allows performing washing steps or elution or dying of the bards.

In yet another aspect of the present invention, the beads are moved by means of a change of the external force responsible of the bead pelleting. Such change may be simply achieved by relative displacement of the tip with respect to the external field force or change of the external force field.

In yet another aspect of the present invention, the tip is filled with beads and different layers of fluids. By moving the beads from a fluid to another fluid, mixing or a change of concentration of one or more substance are achieved within the tip.

In yet another aspect of the present invention, an additional layer of fluids, oils, gels or solutions is added to minimize diffusion among the layers, which the beads must go through during the separation from the fluid solution, generated by difference in density, polarity, miscibility and other chemical and physical properties of the fluids.

In yet another aspect of the present invention, the tip may be pre-loaded with beads which may be magnetic or non-magnetic. The spatial separation is achieved by means of a membrane which is permeable to the fluid, but impermeable to the beads.

In yet another aspect of the present invention, fluid dynamic turbulences are generated inside tip in order to re-suspend the bead cluster without evacuating and evacuating the sample solution or filling the tip with new fluid.

In yet another aspect of the present invention, a washing action is implemented directly inside the tip in order to remove any possible residual of unwanted substance in the bead cluster.

In yet another aspect of the present invention, an elution step is achieved inside the tip in order to allow the removal of the analyte which is attached to the beads.

In yet another aspect of the present invention, the beads are dried out inside the tip in order to remove presence of elution, solvent or any kind of fluid used for the washing or elution of the beads. The drying out can be achieved by movement of fluid or change of temperature of the environment outside or inside the tip.

DETAILED DESCRIPTION OF THE INVENTION

The present invention relates to the manipulation of beads, as well as a number of this applications. For the purpose of illustration, the drawings as well as the description will generally refer to the apparatus and methods addressing this solution of manipulation of magnetic beads in a pipette tip of a liquid handler. However, the means disclosed in this invention are equally applicable to more general embodiments in the field of separation.

Figure 1:
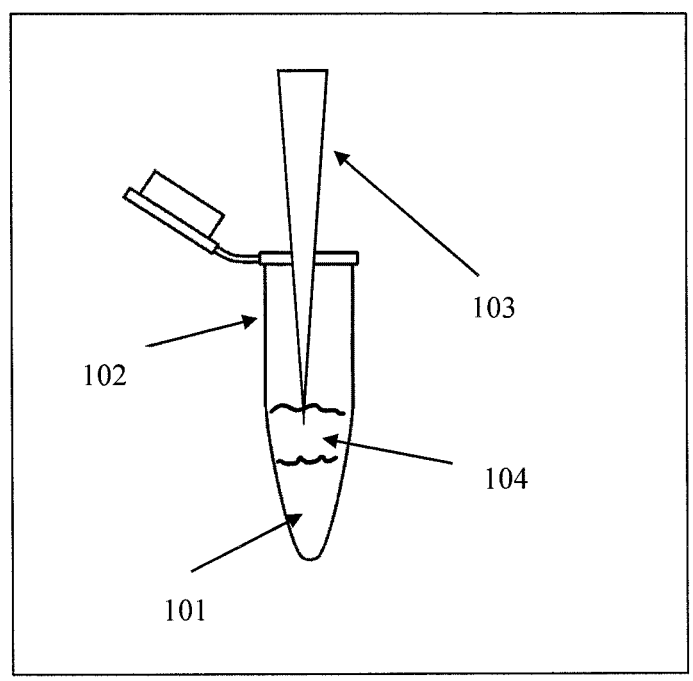
FIG. 1 shows a schematic scenario of the possible shape implementation of the magnetic bead separation using a liquid handler or pipette tip.

General Description of a Displacement and Pelleting of Magnetic Beads in a Liquid Handler Tip FIG. 1 shows a commonly used implementation of the separation of the magnetic beads and the liquid solution using a liquid handler. The beads (101) are pelleted at the bottom of the vessel (102) and the pipette tip (103) aspirate the liquid (104) which does not contain the sample. The positioning of the pipette tip is very important in order to maintain a high collection efficiency and purification efficiency. If the pipette tip is too close to the magnetic bead cluster during aspiration, a small fraction of the beads containing sample may be aspirated by the pipette tip; this causes a decrease of the collection efficiency. If the pipette tip is not closed enough to the bead cluster, unwanted substance is not properly separated from the sample; this causes a decrease of the purification efficiency.

Figure 2:
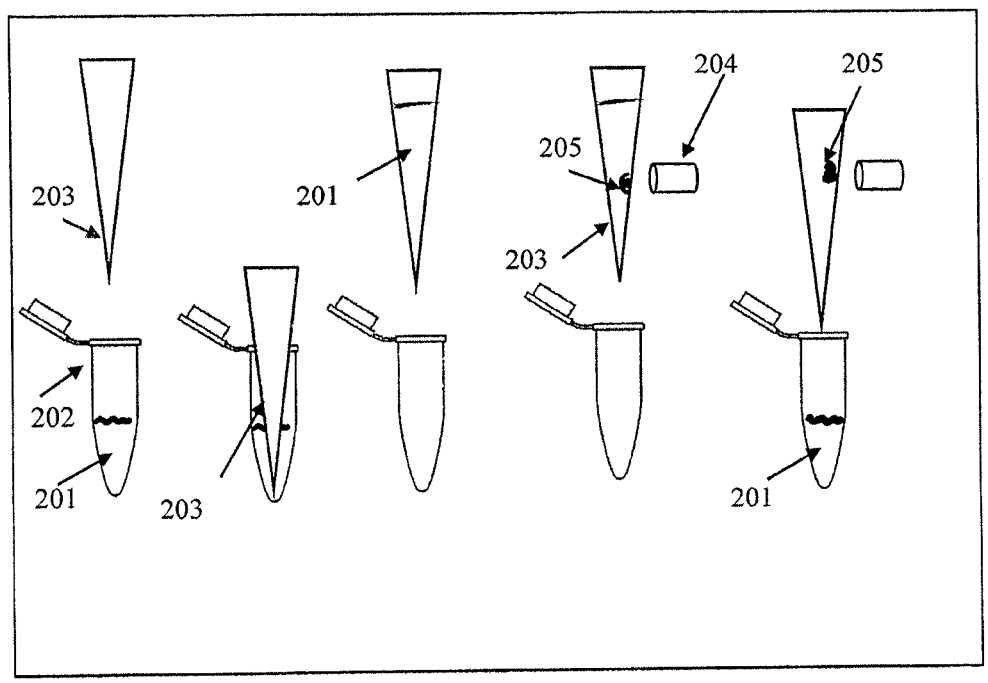
FIG. 2 show a schematic scenario of a magnetic bead separation inside a tip of a liquid handler.

The manipulation of magnetic beads is achieved by means of a homogenous or non-homogenous magnetic field. It is then possible to separate and move a certain number of beads in form of cluster inside and outside the tip of a liquid handler. FIG. 2 shows a possible method and apparatus for the manipulation of magnetic beads in a tip of a liquid handler. In FIG. 2a the sample and magnetic beads (201) are hosted in a vessel (202). This vessel may be optimized in order to optimize the aspiration of the liquid by means of a tip of a liquid handler (203). Initially, the tip is immersed into the sample and the fluid is aspirated by the liquid handler to partially or completely fill the tip, as shown in FIGS. 2b and 2c. Afterwards a magnetic force is applied by means of a permanent magnet, electromagnet or any source of magnetic field (204) to the liquid which is contained by the tip, as shown in FIG. 2d. Under the effect of the magnetic force, the magnetic beads start moving along the magnetic field creating a cluster (205) which contains the analyte. At this point, only the fluid is evacuated from the tip, as shown in FIG. 2e In one embodiment, the bead cluster is kept pelleted and stationary by means of the external magnetic field during the evacuation of the fluid from the tip.

Figure 3:
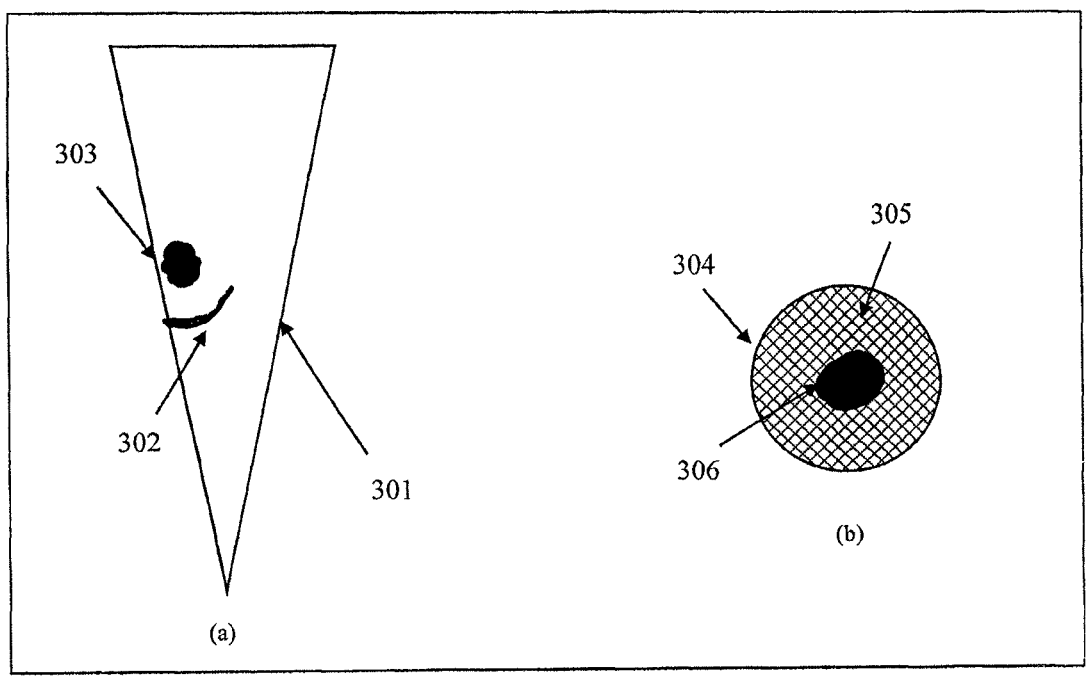
FIGS. 3a and 3b show examples of designs of a tip which is optimized to retain the bead cluster during fluid evacuation from the tip.

In another embodiment, the shape, the dimension, the material or other chemical or physical property of the tip is properly in order to avoid the evacuation of the bead cluster during the dispensing of the unwanted fluid after the separation. In this case the magnetic field may be applied or not applied to the bead cluster. FIG. 3a shows an example of tip (301) designed with a trap (302) for the bead cluster (303), while FIG. 3b shows a tip (304) with a bore (305) designed to block the cluster bead (306) from leaving the tip, but allowing the fluid from entering and leaving the tip.

In yet another embodiment, the beads are properly designed or selected in such a way that their coercivity and their cohesion forces, with or without the use of an external force, are bigger than the turbulences created by the evacuation of the fluid from the tip.

Figure 4:
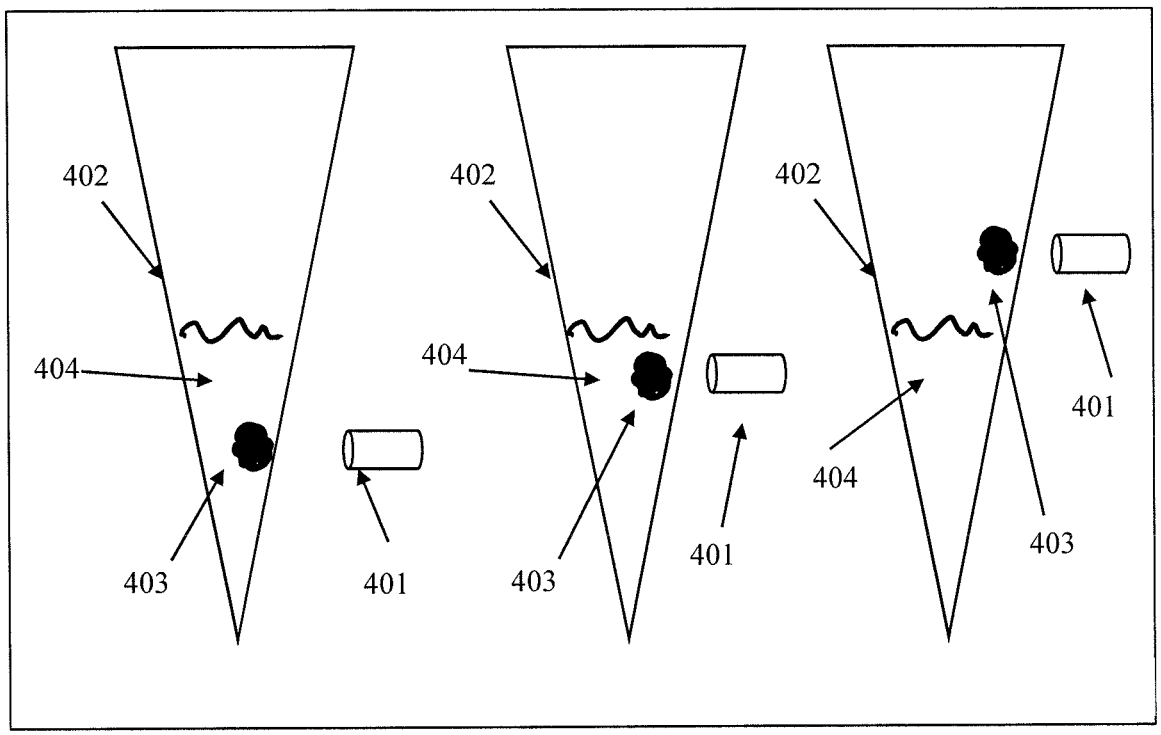
FIG. 4 shows the displacement of a bead cluster inside the tip. The cluster is taken out from the fluid present inside the tip.

General Description of a Displacement and Pelleting of Magnetic Beads in a Liquid Handler Tip with Multi-Layer of Fluids In one aspect of the present invention, the bead cluster is taken out from the fluid by an action of the liquid handler and the external force. In FIG. 4 a sequence of images shows how a relative displacement between the source of the magnetic force (401) and the tip (402) may result as a movement of the cluster bead (403) inside the tip. By means of this movement, the bead cluster can be completely moved out from the fluid (404). In this scenario, the turbulences created by the evacuation of the fluid from the tip does not affect the position and the integrity of the bead cluster.

In another embodiment, a certain amount of one or more fluids, gels or solutions are aspirated inside the tip before aspirating the solution containing the bead or the analyte. Such layers may be chosen on purpose in order to minimize the potential barrier which the beads must go through during the separation from the fluid solution.

In yet another embodiment, by means of a precise control of the amount of volume which the liquid handler can aspirate or dispense, the evacuation or formation of layers made of fluids, gels or solutions may be added to or removed from the tip before, after or during the aspiration of the beads.

In yet another embodiment, an air cushion is added to the tip before or after the aspiration of a certain fluid. The purpose of such air cushion is to minimize the possible diffusion, mixing or contamination between consecutive fluidic layers in the tip.

General Description of Washing Step of Beads in a Liquid Handler Tip

Figure 5:
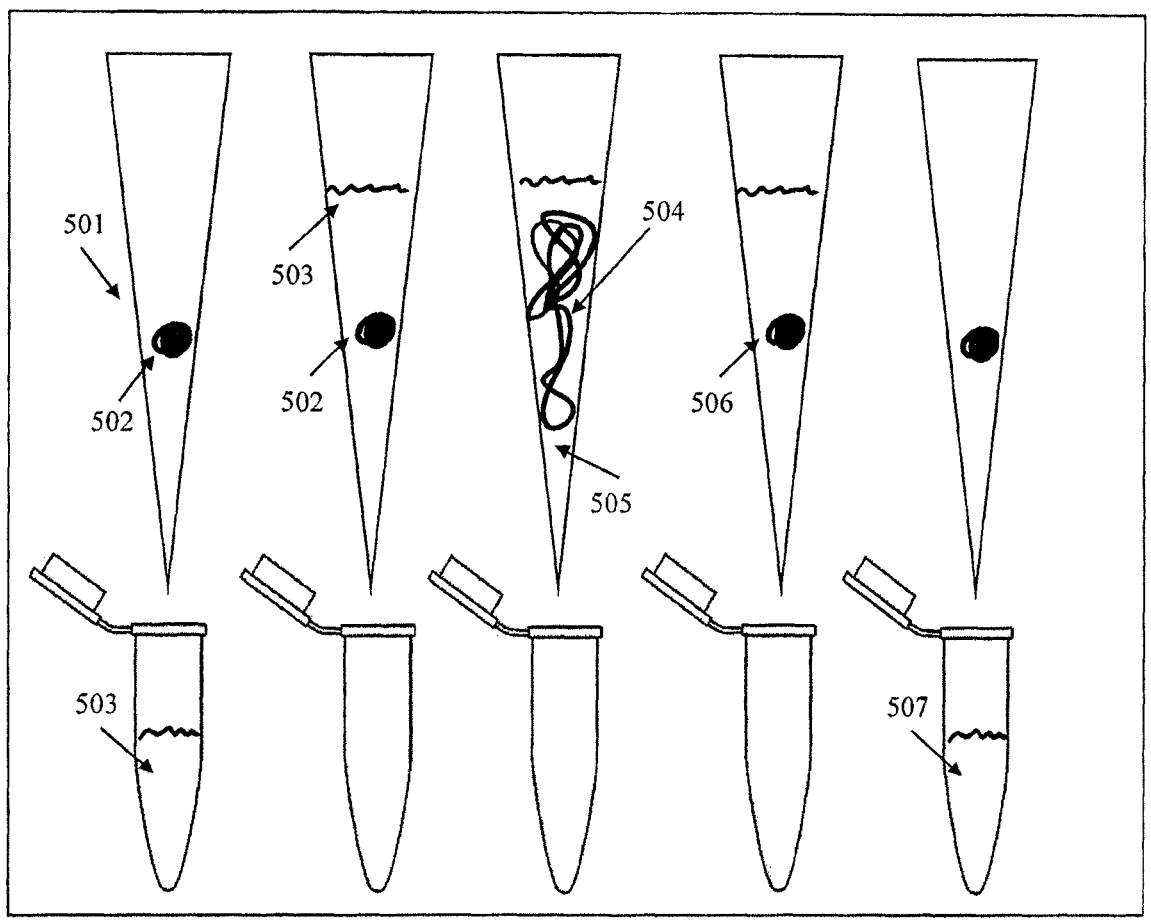
FIG. 5 shows the implementation of the washing step inside a tip of a liquid hander.

To enhance the purification efficiency of the separation, it is possible to implement one or several washing steps in order to remove possible presence of unwanted substance or fluids still present after the evacuation of the fluid. FIG. 5 shows a possible method and apparatus for the washing of magnetic beads in a tip. In FIG. 5a, the tip (501) of a liquid hander is shown and contains a cluster of beads (502) previously pelleted. FIG. 5b shows the washing buffer (503) entering the tip during aspiration and the bead cluster is immersed in the washing buffer.

In one embodiment, the beads are kept pelleted during the washing step and the washing buffer is simply aspirated and dispensed one or several times.

In another embodiment, the beads are re-suspended in order to enhance the removal of the unwanted substance which may be trapped inside the bead cluster, as shown in FIG. 5c, where the beads in cluster (504) are dispersed into fluid (505) and detached from the tip surface. In this case, the bead cluster (506) must be recreated, as shown in FIG. 5d and the washing buffer containing unwanted substances (507) is evacuated from the tip (FIG. 5e).

General Description of Washing Step of Beads with Pre-Loaded Buffer in a Liquid Handler Tip In one embodiment, the washing buffer may be pre-loaded inside the tip (e.g. pre-aspiration) in a form of fluid layer ready to be used after the evacuation of the fluid.

In another embodiment, washing and elution buffers are flushed though the tip by switching into a dispensing mode of a dispenser.

General Description of Drying Out of Beads in a Liquid Handler Tip

In one embodiment, the beads are dried out in order to remove any presence of residual washing buffer or unwanted substances which may contaminate the analyte.

In another embodiment, the tip that contains the beads is heated in order to enhance the drying of the beads". In yet another embodiment, a gas is flushed through the tip in order to evacuate the liquid. The gas can be cold, warm, hot or at room temperature depending on the application requirements.

General Description of Resuspension of Magnetic Beads Inside A Tip

In one embodiment, the resuspension of the magnetic beads is carried out by turbulences generated by the fluid entering and exiting the tip of the liquid hander. The fluid flow rate can be optimized in order to enhance the effect of the shearing force and overwhelm the cohesion forces of the bead cluster.

In yet another embodiment, the tip is properly designed in order to enhance and increase the effect of shearing forces generated by the fluid moving inside the tip.

In yet another embodiment, an external magnetic, acoustic, electromagnetic, mechanical or thermal force is applied to the tip or directly to the bead cluster in order to resuspend the beads.

General Description of Elution of Beads Inside a Tip

In one aspect of the present invention, the elution of the analyte bound to the beads is carried out directly inside the tip by aspirating the required elution buffer which must wet the beads.

In another embodiment, the resuspension of the bead cluster is carried out after placing the beads in contact with the elution buffer. The resuspension of the beads may take place inside the tip of the liquid handler or inside another container.

General Description of Bead Separation Using Pre-Loaded Tip

Figure 6:
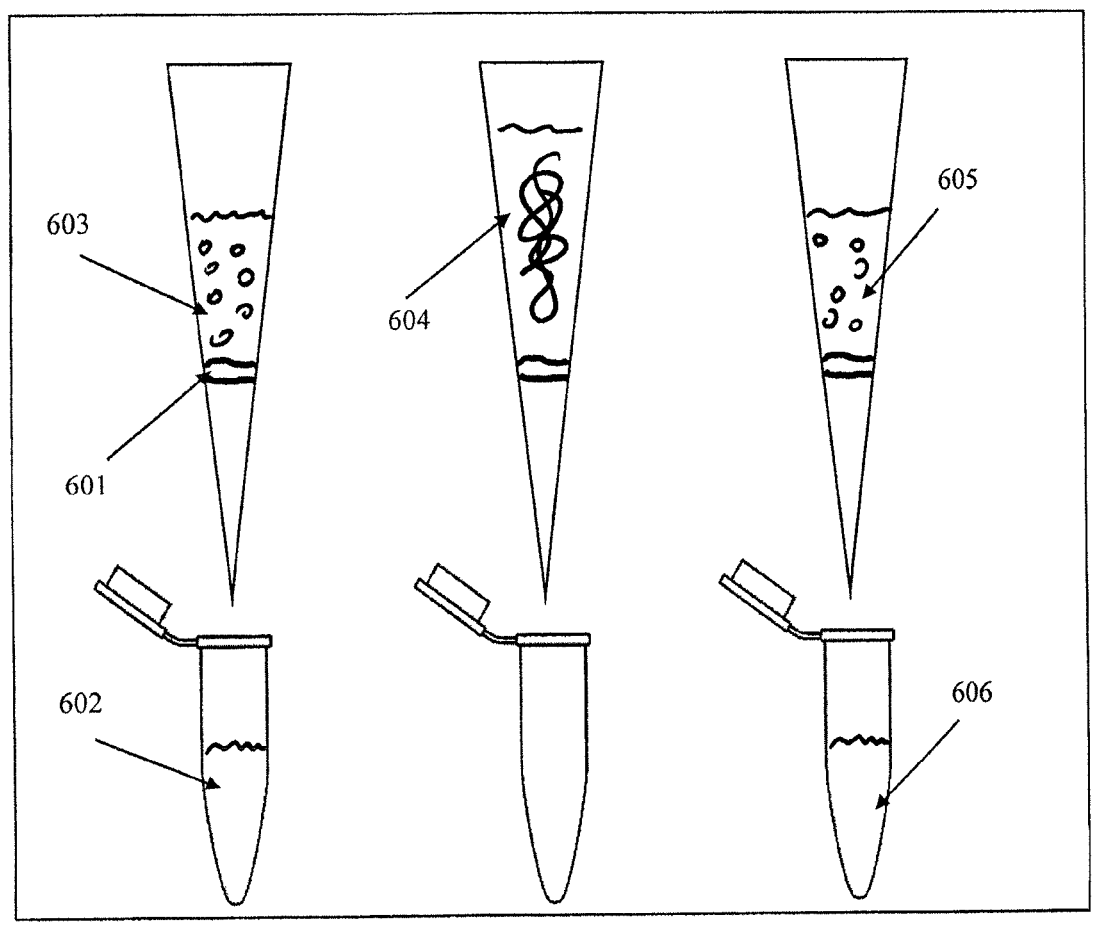
FIG. 6 shows the bead separation with the use of pre-loaded bead and a membrane inside the tip.

In yet another aspect of the present invention, the tip is pre-loaded with beads which may be magnetic or non-magnetic, as shown in FIG. 6a. The tip contains a membrane (601) which is permeable to the sample solution (602), but not to the beads (603). FIG. 6b shows the tip after the aspiration of the sample solution. The analytes are bounded to the beads on the top of the selective membrane. In order to separate the beads containing the sample (605) from the remaining fluid solution (606), liquid handler simply evacuates the fluid from the tip. The membrane selectively creates a barrier for the beads, while the solution can evacuate the tip.

To collect the sample from the beads, it is necessary to aspirate a solution which is responsible to detach the analyte from the beads. During the consecutive dispensing, the analytes, but the beads, are evacuated from tip since the membrane is permeable to them General Description of Optimal Trajectories Entering or Exiting Magnetic Field In general, the motion of the beads is achieved by the change of an external force acting on the beads. This change of force, for example, can be achieved by the activation of an electromagnet.

In another implementation, the change of the forces applied to the beads is achieved by the simple process of displacing the tip. The trajectory of the tip with respect to the external static field may affect the way the beads are collected and dispersed within the fluid.

In one aspect of the present invention, the trajectories to enter or leave the magnetic field are optimized in order to avoid delocalization of the bead cluster or unwanted resuspension of the beads. The approaching trajectories to the magnetic force source are designed to follow the lines of the magnetic field. Similarly, in order to avoid perturbation of the bead cluster, the leaving trajectories are design to follow the lines of the magnetic field or to move to orthogonal directions.

For example, when the beads are in a static situation where the external force is pushing the cluster against the wall of the tip, moving the tip in such a way that the external force will change in intensity but maintain the same direction will favour the persistence of the aggregate onto the tip wall, while a movement where the external force changes direction and pushes the beads away from the wall may favour resuspension. Further, a region where a field is rapidly converging may favour aggregation of the cluster, while a divergent region may favour resuspension of the cluster.

General Description of Optimal Removal of Residuals of Washing Buffer

In general, the magnetic beads before the elution step must be free from the presence of washing buffer. In fact, even a small contamination of washing buffer may interfere with subsequent analysis of the analyte. Drying out of the magnetic beads may not be sufficient, in particular and it may be a relative long process. In order to guarantee a non-contaminated analyte after the bead separation process, washing buffer residuals inside and outside the pipette tip are removed before the elution step.

Figure 7:
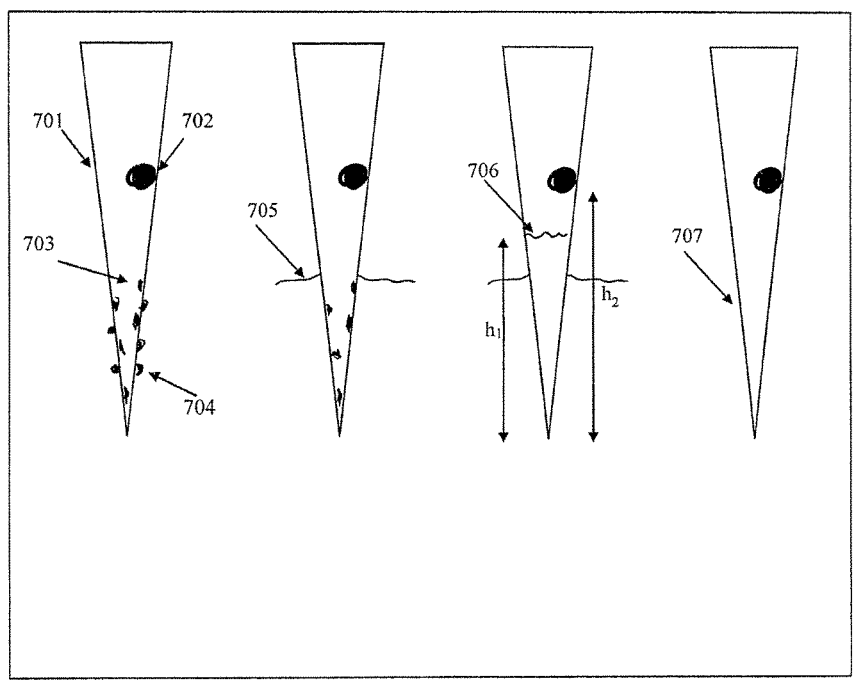
FIG. 7 shows a schematic scenario of the removal of residuals of washing buffer from the pipette tip.

In FIG. 7 a sequence of images shows how a pipette tip (701) carrying out a beads (702) can be cleaned up from residuals of washing buffer present inside the tip (703) and outside the tip surface (704). The removal of the washing buffer residual inside and outside the pipette tip is achieved by aspirating a predefined volume of the wiping fluid (706).

Typically, the amount of volume is chosen in order to have the height of the column of the wiping fluid inside the tip shorter than the height at which the beads are pelleted. Nevertheless, any amount of wiping fluid volume may be used, in particular if the inertia between the beads and the wiping fluid is verified. By purging the wiping fluid from the pipette tip (707), the possible presence of washing buffer is removed.

In one implementation, the pipette tip is immersed in a wiping fluid (705) in order to remove possible residuals of washing buffer from the external surface of the tip. In yet another implementation, the removal of washing buffer residuals is optimized by moving the pipette tip inside the solution. In yet another implementation, the tip is immersed in a wiping fluid and the removal of the washing buffer residuals is optimized by means of a stirrer, mixer, sonicator, agitator or any device which generated a turbulent or laminar flow of the fluid around the pipette tip.

General Description of Storage of Pipette Tip Containing Bead Cluster

In another implementation, the tip containing the pelleted beads is removed from the pipette and stored in a suitable rack for subsequent or parallel processing of the analyte. The rack containing the tip may be equipped a fixed or variable magnetic field in order to keep the beads pelleted.

In yet another implementation, the stored tips containing the pelleted beads undergo a process of drying out the washing buffer after washing step. The drying out of the beads may be achieved by movement of fluid, change of temperature of the environment outside or inside the tip or by electromagnetic irradiation.

General Description of Movement of the Beads to Avoid Cross-Contamination Among Samples In general, the magnetic force depends on the distance from the magnet. For this reason, in order to maximize the collection efficiency, the pipette tip must be as close as possible to the magnet. Nevertheless, the contact between the magnet and the tip may be not possible if the cross-contamination among samples must be avoided. In general, a portion of the tip is immersed in the fluid containing the analyte during aspiration and dispensing which may depend on the quantity of the liquid to aspirate. For this reason, the external surface of the portion of the tip immersed in the solution may carry over some liquid residuals which may contaminate the surface of the magnet. If the tips are put in contact to the magnet in order to maximize the collection efficiency, cross-contamination among samples may occurs. A simple solution to avoid cross-contamination among samples, if to put the magnet in contact only with the portion of the tip which is not immersed in the liquids during liquid handling operation.

In one implementation, the pelleted beads are swept along the pipette tip using an external magnetic field in order to reach the portion of the tip which is not immersed in the liquids and which can be safely put in contact with the magnetic in order to maximize the collection efficiency without occurring into contamination issues.

In another implementation, the liquid containing the beads is aspirated inside the pipette tip in order to reach the position of the tip which is not immersed in the liquid during liquid handling operation. Successively, the pelleting of the beads occurs in the same position inside the tip.

In another implementation, the surface of the magnet which is placed in contact with the pipette is clean up in order to remove any possible present of contamination.

Figure 8:
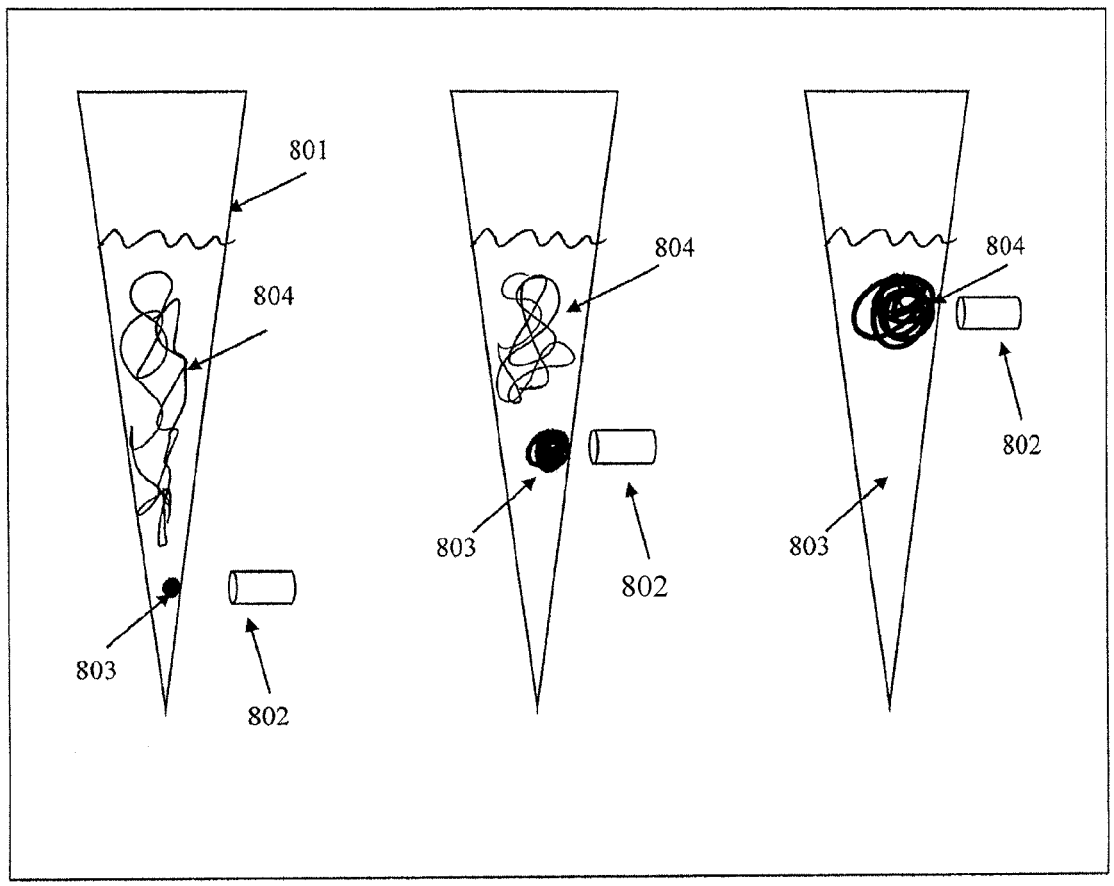
FIG. 8 shows a schematic scenario of the implementation of the dynamic sweep during the bead collection.

General Description of Dynamic Sweep of the Pipette Tip During the Collection of Beads In another implementation, the collection of the beads is carried out by a relative dynamic sweep of the pipette tip with respect of the position of the magnet. In fact, the mutual and cooperative interaction between the magnetic beads is exploited in order to enhance their collection in the whole tip. In FIG. 8 a sequence of images shows how a possible dynamic sweep of the pipette tip (801) with respect to a magnet (802) in order to use the bead cluster (803) to collect all the remaining floating beads (804) inside the sample solution.

General Description of Optimized Gradient of the Magnetic Field

In other implementation, the gradient of the magnetic field is designed in order to optimized the collection efficiency of the magnetic beads by exploiting a combination of different profiles of the magnetic field. In particular, one or a combination of magnetic field profiles may be used in order to concentrate the beads in a small region to create a compact cluster, whereas one or a combination of magnetic field profiles may be used to collect the beads present in the entire pipette tip and move them in the region where the total magnetic field gradient has its maximum.

Figure 9:
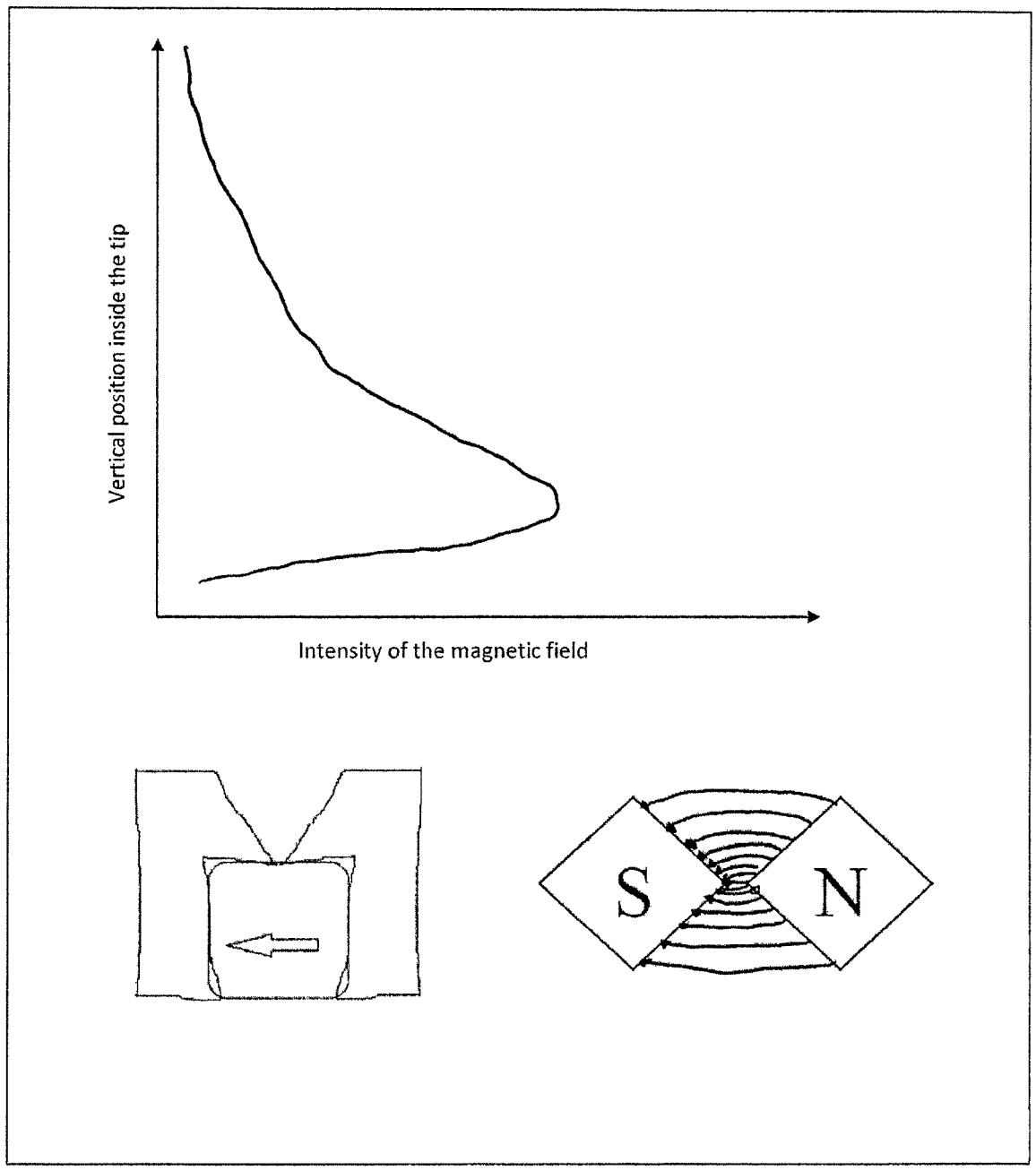
FIG. 9 shows the graph of a possible optimized magnetic field profile for the collection of the beads and possible optimized magnetic configuration.

In FIG. 9 a possible implementation of an optimized gradient of the magnetic field along the vertical axis of the pipette tip is shown.

General Description of Beads Resuspension and Mixing Inside the Pipette Tip

In general, the resuspension of the magnetic beads and the mixing are carried out outside the pipette tip by repeatedly transferring a mixture of the liquid and magnetic material between a vessel and the pipette tip. Nevertheless, such method may implicate possible losses of the beads or contamination for external factors. In particular, in case of automated liquid handler, a small amount of liquid cannot be aspirated according to the positioning of the pipette tip inside the consumable, the geometry of the consumable and the properties of the material which the consumable is made of (e.g. hydrophilicity). To minimize possible losses of beads and contamination the magnetic beads are re-suspended and mixed directly inside the pipette tip.

In one implementation, the resuspension of the beads is carried out by dynamically applying an external magnetic field which causes the shearing of the bead clusters. In another implementation, the mixing of the beads with binding buffer, washing buffer and elution buffer is carried out by dynamically applying an external magnetic field which causes the migration of the beads inside the liquid.

In yet another implementation, the external magnetic profile is designed in order to exploit the internal well of the tip during the re-suspending and mixing of the beads inside the pipette tip.

General Description of Drying Out of Beads in a Liquid Handler Tip

In yet another embodiment, the pipette tip repeatedly aspirates and dispenses gas in order to dry out the beads. During such procedure, the pipette is being moved in order to avoid a possible aspiration of pre-evacuated gas which now contains vapor or aerosol of the washing buffer.

General Description of the Mixing Between Bead Cluster and Liquid Inside the Tip In general, it may happen that the volume used for the elution buffer is small in order to have a relative high final concentration of the analyte after the separation procedure. For this reason, the bead cluster may be created at a vertical position inside the pipette tip which is higher than the height of the liquid column of the elution buffer. A possible method is to use an air gap at the bottom of the tip to move vertically move the liquid in order to put it in contact with the bead cluster.

Figure 10:
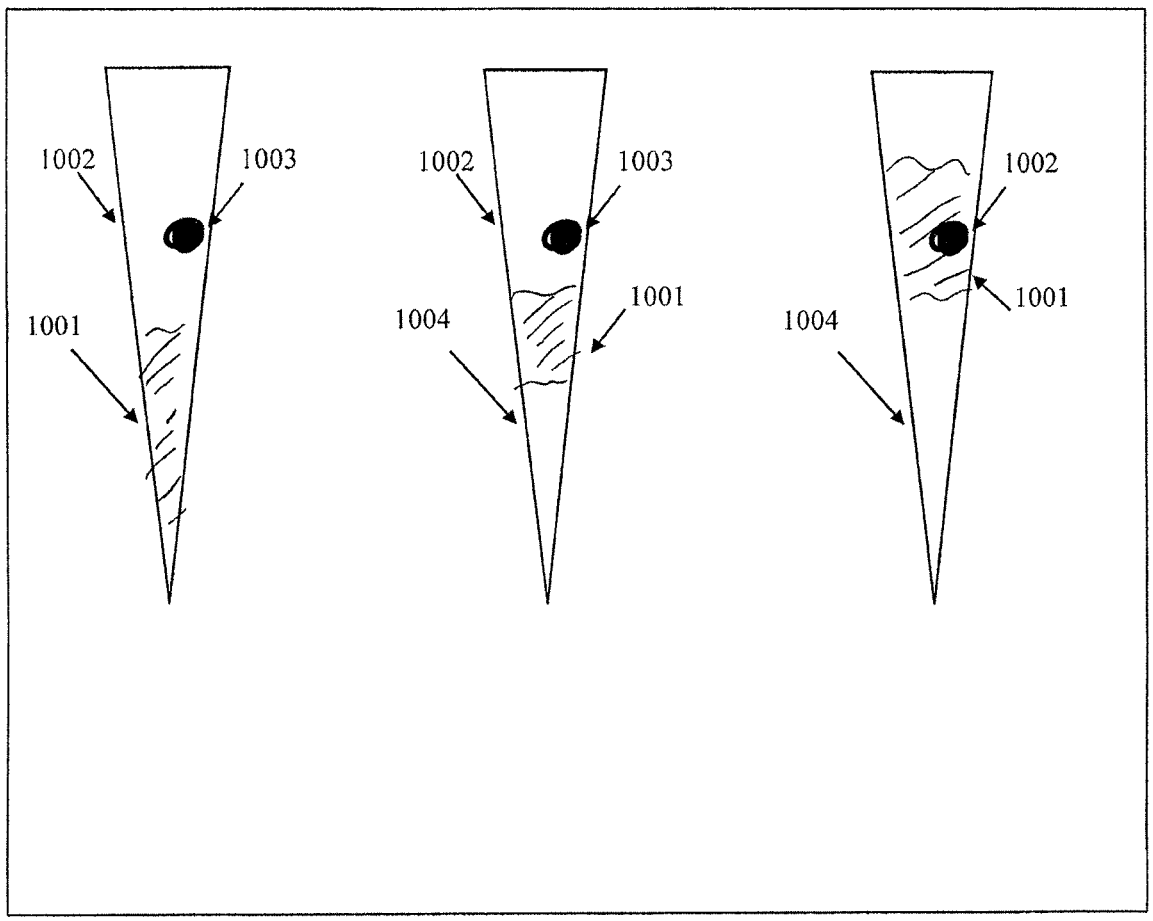
FIG. 10 shows a schematic representation of the use of air gap to move the liquid in contact with the bead cluster.

In FIG. 10 a possible implementation of the use of the air gap inside the pipette tip in order to put liquid in contact with the cluster of beads. The amount of liquid (1001) presents inside the pipette tip (1002) is not sufficient to wet the bead cluster (1003). By creating an air gap (1004) at the bottom of the pipette tip, the liquid previously aspirated is forced to move towards the bead cluster.

In another embodiment, the bead cluster by applying an external magnetic field is force to move toward the liquid present in the tip.

General Description of the Use of Detergent During the Bead Separation

The relative movement of the liquid present in the pipette tip and the bead cluster may perturbate the agglomeration of the bead causing a possible detachment of a certain number of beads. The loss of such beads may cause a decrease of the collection efficiency or a contamination of beads during the elution step. Use of detergent (e.g. Tween-20, Triton X-100) minimize the hydrodynamic turbulences undergone during the evacuation or aspiration of the liquid.

General Description of Iterative Bead Collection

Figure 11:
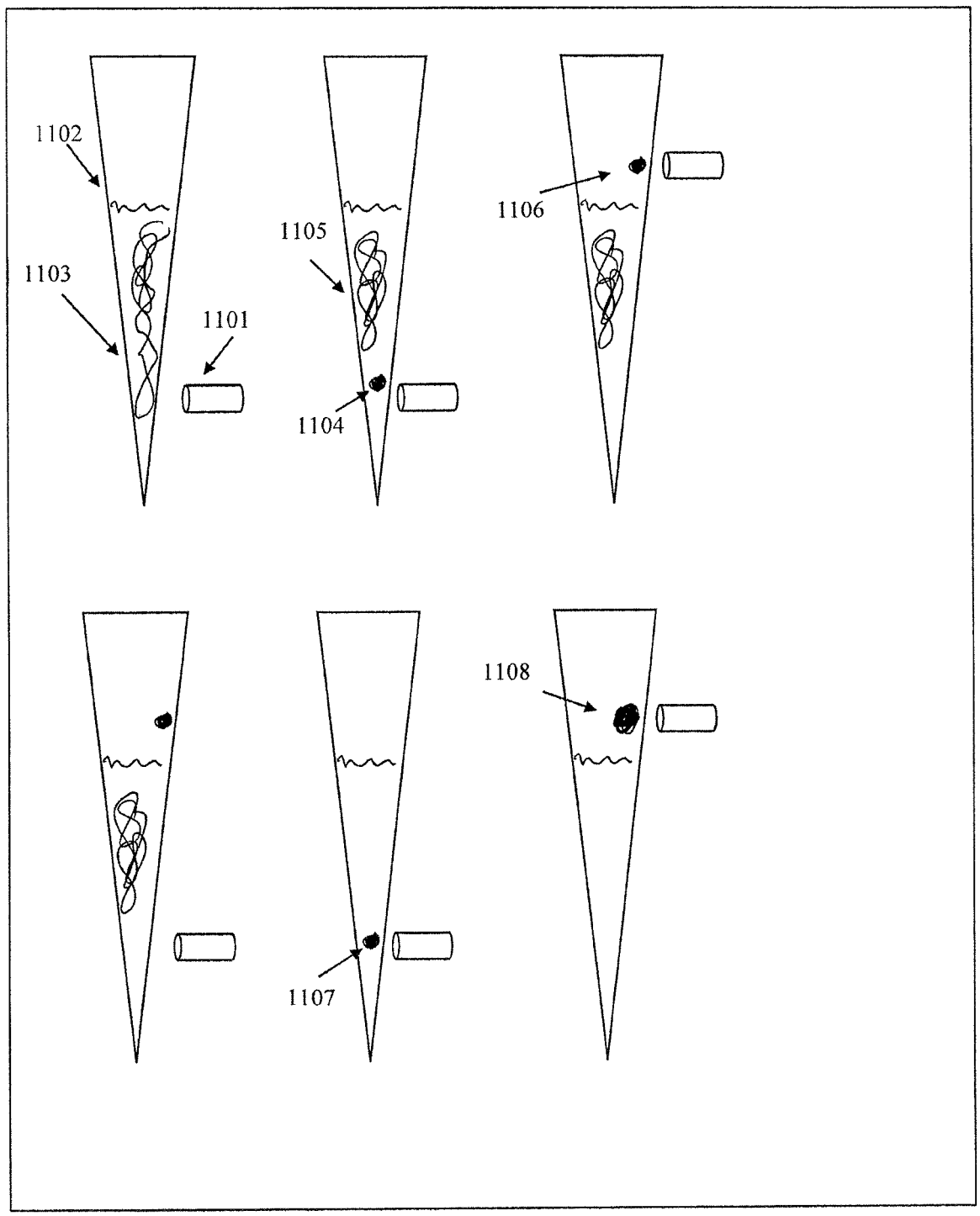
FIG. 11 shows a schematic scenario of possible iterative bead collection inside a pipette tip.

Magnetic field saturation and very localized magnetic field gradient may be a limitation for the collection of magnetic bead. For example, if the volume of the bead cluster is higher that the region where the magnetic field gradient is applied, the hydrodynamic turbulence of the relative movement of the liquid inside the tip may cause possible losses of some beads. In one implementation, the process of formation of the bead cluster and its movement away from the liquid is carried out repeatedly as shown in FIG. 11. The magnet (1101) is put close to the pipette tip (1102) which contains the solution with beads (1103). The first bead cluster is created (1104) while the remaining about of beads (1105) stays in the solution. The cluster of beads (1106) is then removed from the liquid. Afterwards, the process is repeated by creating a new bead cluster (1107) which is removed from the liquid and it will be merged with the previous cluster creating a new bigger bead cluster (1108)

General Description of Feedback System for Bead Collection

In one implementation, a feedback system is generated in order to optimize and verify the efficiency during the collection efficiency. A sensor is placed relative close to the pipette tip during the pelleting and resuspension of the magnetic beards.

In one embodiment, the sensor is a vision-based system which detect the creation or resuspension of bead cluster by image processing. In another embodiment, the optical density of the liquid present in the pipette tip is measured in order to identify the pelleting and resuspension of the beads.

Isolation and purification of biomolecules (double- and single-stranded DNA, total RNAs, mRNAs, miRNA, proteins), as well as specific cells and organs, facilitate a wide array of downstream applications in gene and protein expression studies, cloning, transfection, protein-protein interactions, immunology, clinical diagnostics, cDNA library synthesis, PCR and qPCR, Sanger and NGS sequencing, and more. Due to its simplicity, recovery efficiency and purity, magnetic separation has found its place in this bio-separation arena and gradually replaced the traditional liquid phase and solid phase separation methods, which require extensive centrifugation or vacuum filtration, and are not amenable to automation.

However, several factors hinder the magnetic separation from becoming a main-stream method as duly expected. First, the samples for purification are collected in a variety of consumables, from 384-, 96-, and 24-well plates to small, medium, and large tubes, all in different shape and volume capacity ranging several microliters to milliliters. Traditionally, a realm of diverse magnetic separators has, therefore, been developed in all shapes and sizes to accommodate different consumables. Buying a specific magnetic separator for each application can quickly become very costly. Second, good recovery efficiency requires attentive pipetting technique that avoids disturbing the bead pellets in order to prevent bead loss during the isolation and washing steps and bead contamination during the final elution, which is time-consuming and not reproducibly achievable. Third, to ensure bead cleanliness or high recovery of biomolecules at the final step, homogenous magnetic bead resuspension after pelleting is achieved by intensively repetitive pipetting. This task significantly increases the risk of muscular skeletal disorder named repetitive strain injury for scientists and technicians, in addition to their loss of hands-on time manually performing the magnetic separation protocols.

All of these barriers can now be removed with the innovative design of automatic magnetic bead separation technology according to the disclosure. This platform includes a One-Size-Fit-All magnetic separator handled by the bench-top pipetting robot Andrew to execute all bead manipulation steps within the pipet tips, including liquid aspiration, bead mixing with samples, bead washing, bead pelleting, incubation, drying, and sample elution. Completely independent of the consumables holding the samples, scalable for all common volume ranges of biological applications, with adjustable and optimizable parameters for bead manipulation suiting each and every protocol, the apparatus according to the disclosure will consistently achieve sample recovery above 84% and up to 99%, contaminants-free and ready for downstream applications.

Examples

Efficient Automatic PCR Purification with BeadTender

Often PCR products need to be purified to remove contaminants (unincorporated dNTPs, left-over primers, primer dimers less than 100 bp, salt, and enzymes) before being used for cloning, transfection, or Sanger sequencing. We tested the purification efficiency by BeadTender of PCR products generated with the KAPA HiFi HotStart ReadyMix PCR Kit (KAPA). Multiple reactions were pooled and split into six 20 µL or 50 µL samples. A pipetting robot Andrew Alliance model 1000R used the XTips 250 µL (Biotix), the L100 and L200 pipettes for handling the 20 µL samples in the 0.2 mL PCR tubes and 50 µL samples in the 1.5 mL microcentrifuge tubes, respectively. 36 µL or 90 µL of RXN Pure magnetic beads (Omega Biotek) were mixed by Andrew with 20 µL or 50 µL samples. The bead pellets were washed twice with 100 µL or 150 µL 80% EtOH and once with 100 µL or 150 µL water, and the purified PCR products were eluted in 20 µL or 50 µL 10 mM Tris buffer (pH 8) as six replicates P1-P6, all automatically performed by Andrew.

Figure 12:
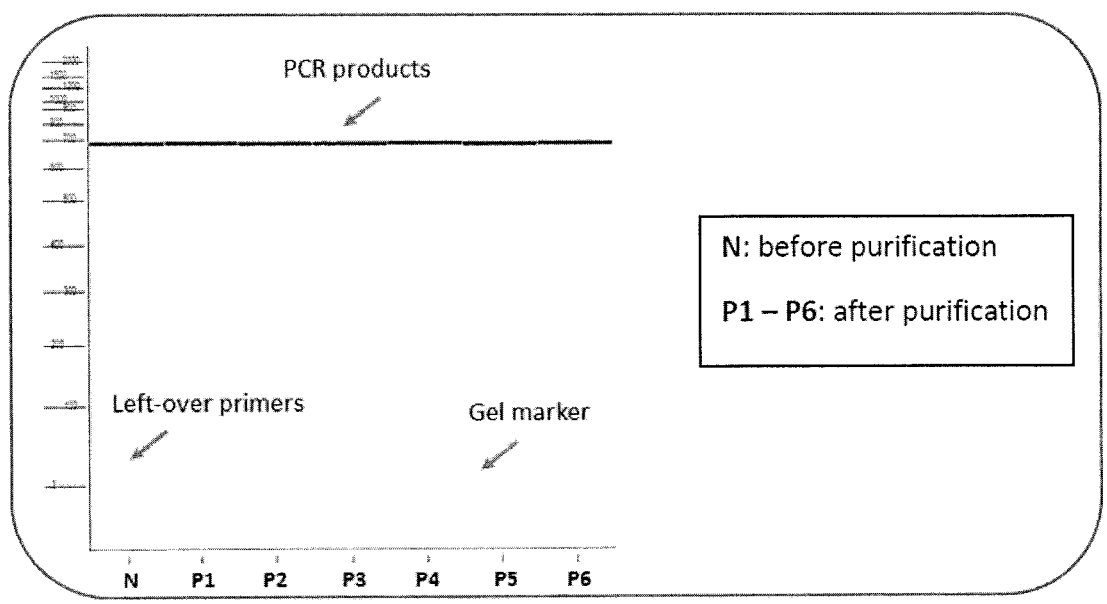
FIG. 12 shows complete removal of primer contaminants in PCR products purified by apparatus according to the disclosure.
Figure 13:
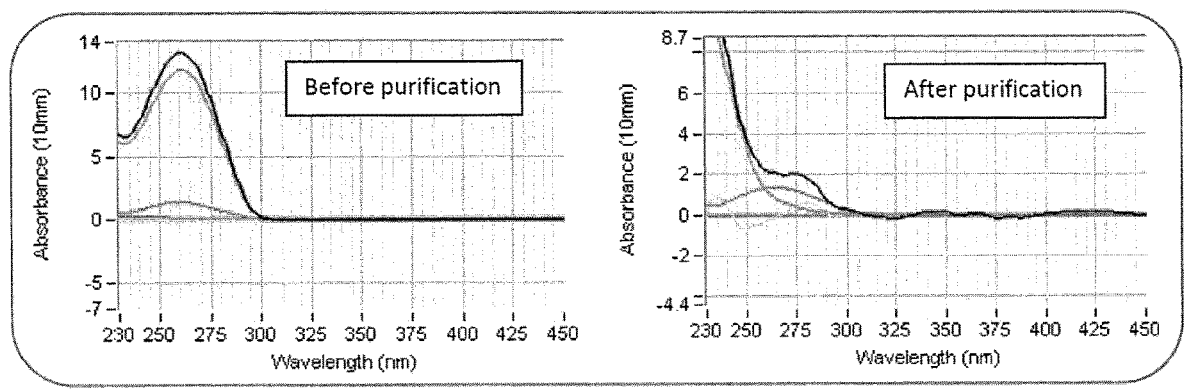
FIG. 13 shows no bead contamination in final PCR products cleaned up by according to the disclosure.
Figure 14:
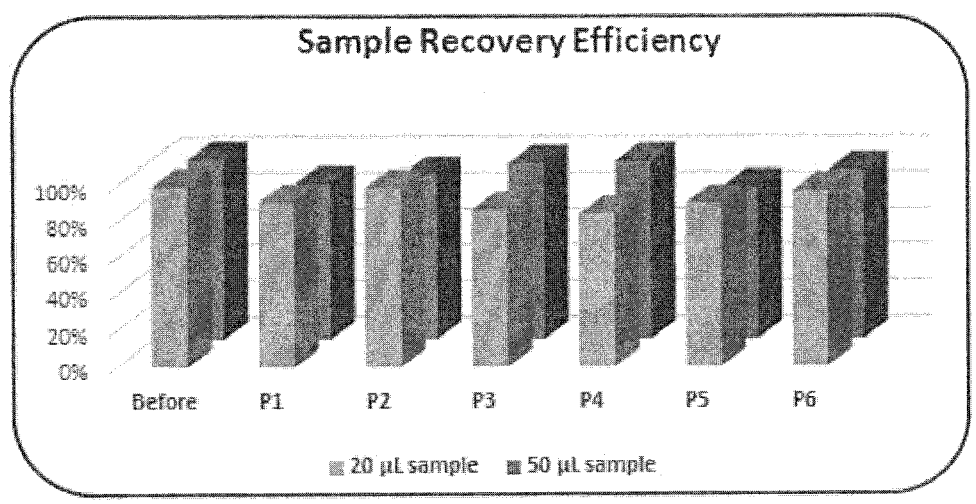
FIG. 14 shows sample recovery efficiency performed according to disclosure.

Qualitative and quantitative assessment of the purification demonstrate that BeadTender effectively recovered all samples free of contaminants (FIGS. 12-13) with superior yield (Table 1, FIG. 14). µL of samples before and after purification was analyzed by capillary electrophoresis in a Fragment Analyzer (Advanced Analytical Technologies). The lower gel marker was loaded in all samples for reference. No contaminants of <100 bp (primers and primer dimers) remained in any of the purified PCR products for both 20 µL and 50 µL samples. µL of each sample before and after purification was measured for bead and other impurities with the spectrophotometer Dropsense16 (Trinean). No indication of bead contamination was found in any cleaned up samples.

TABLE 1

| | Sample recovery efficiency performed by BeadTender | | | | | | |
|---|---|---|---|---|---|---|---|
| | Before | After purification | | | | | |
| 20 µL sample | pooled | purified 1 | purified 2 | purified 3 | purified 4 | purified 5 | purified 6 |
| Concentration (ng/µL) | 32.4 | 29.6 | 32.2 | 28.2 | 27.4 | 29.4 | 31.6 |
| Recovery efficiency | | 91.4% | 99.4% | 87.0% | 84.6% | 90.7% | 97.5% |
| 50 µL sample | pooled | purified 1 | purified 2 | purified 3 | purified 4 | purified 5 | purified 6 |
| Concentration (ng/µL) | 32.2 | 27.8 | 29.4 | 31.4 | 31.8 | 27.2 | 30.2 |
| Recovery efficiency | | 86.3% | 91.3% | 97.5% | 98.8% | 84.5% | 93.8% |

Figure 15:
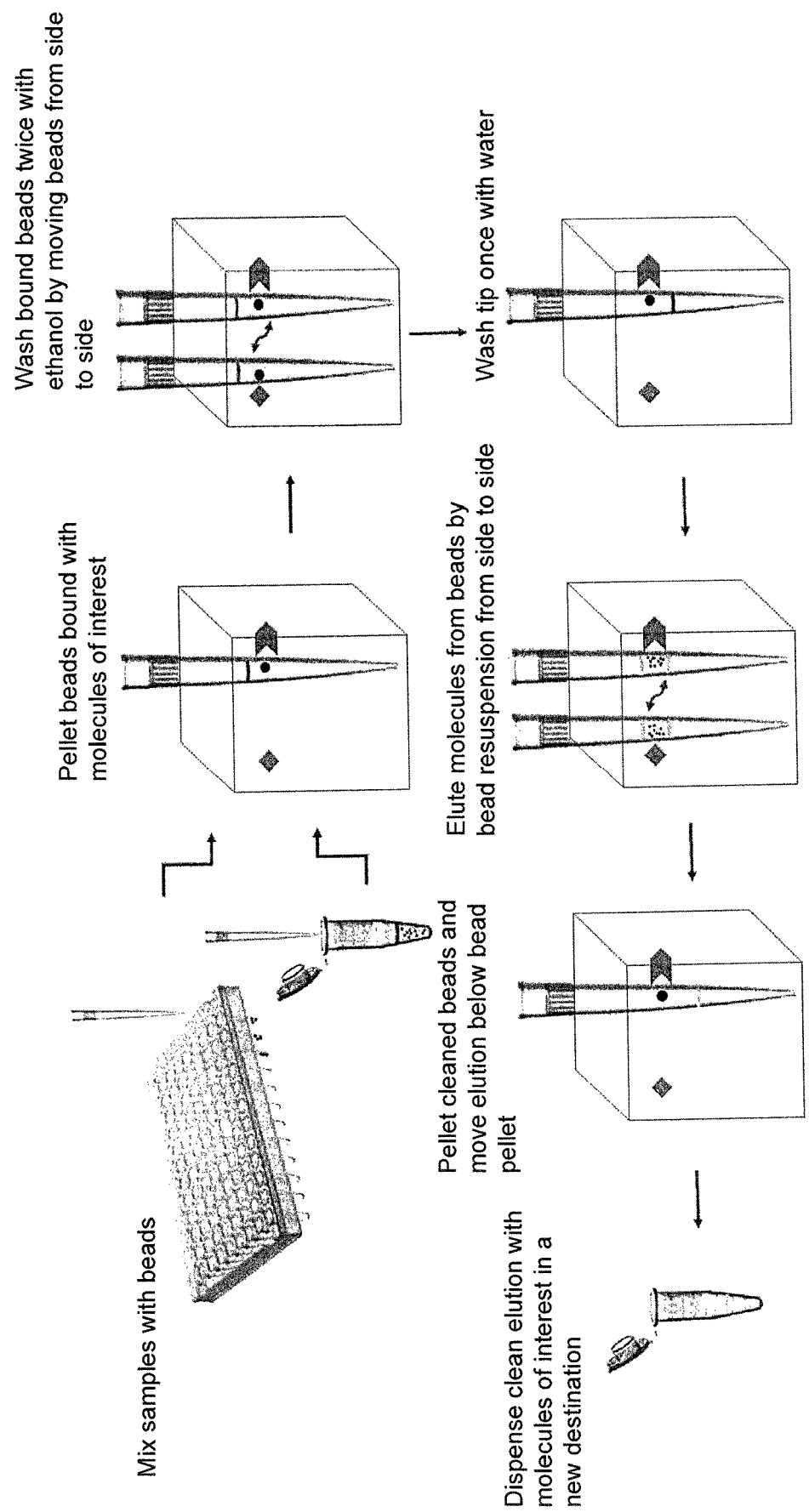
FIG. 15 shows workflow of magnetic separation according to disclosure.

1 µL of each sample before and after purification was measured with the fluorometer Qubit using the HS DNA quantitation kit (ThermoFischer Scientifics). The percentage of recovered PCR products in six purified replicates (P1-P6) for 20 μL and 50 μL samples was calculated with respect to the concentration of the pooled PCR before purification (Table 1). All samples were consistently recovered at 84%-99%. The workflow of magnetic separation by BeadTender is contained entirely within a single pipet tip as shown in FIG. 15, which accommodates samples as low as 5 μL and as high as 5 mL depending on the applications. The process starts in any consumable of users' choice where samples are mixed with the appropriate magnetic bead type for capturing the biomolecules of interest (FIG. 15A). The sample-bead mixture is aspirated into a pipet tip, which is moved to a magnet of BeadTender to pellet the beads (FIG. 15B). After the supernatant is cleared of beads and discarded, the same tip draws ethanol in and moves between the two magnets of BeadTender to wash the bead pellet (FIG. 15C). Next, ethanol is discarded and water is aspirated into the tip below the bead pellet to remove ethanol trace, and the pellet inside the tip is dried by air blown through the tip via the pipette thumb's periodic vertical movement (FIG. 15D). Elution buffer is then drawn in with an air cushion at the tip bottom to effectively cover the bead pellet, and the biomolecules are released from the beads by pellet resuspension achieved via moving the tip between the two magnets of BeadTender (FIG. 15E). The cleaned beads were pelleted and separated from the elution containing the biomolecules (FIG. 15F), which were finally transferred to a new destination consumable (FIG. 15G). The complete process is carried out by the pipetting robot Andrew. Users only need to supply the samples, beads, wash buffers, elution buffer of choice, and clean consumables for the final purified products.

The pelleting time as well as bead resuspension and duration are entirely adjustable in the graphical software Andrew Lab according to the bead types, sample viscosity, and ionic force and pH of the buffers, giving users total flexibility and control to optimize any protocols for highest and reproducible sample recovery efficiency and purity.

The specification is most thoroughly understood in light of the teachings of the references cited within the specification. The embodiments within the specification provide an illustration of embodiments of the invention and should not be construed to limit the scope of the invention. One skilled in the art readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following appended claims.

What is claimed is:

1. A method for separating beads within a tip of a liquid hander, comprising:
    aspirating a liquid containing beads into the tip, wherein at least some beads have magnetic properties;
    applying a magnetic field to at least a portion of the tip volume;
    varying the magnetic field applied onto the tip volume over time, whereas one or more magnetic field profiles provide an optimized gradient of the magnetic field along a vertical axis of said tip;
    separating the magnetic beads from the liquid into a bead cluster by action of the optimized gradient of the magnetic field; and
    dispensing the liquid from the tip without evacuating the magnetic beads.

2. The method according to claim 1, wherein the magnetic beads are separated from the liquid inside the tip by means of accumulation of magnetic beads on a previously separated bead cluster.

3. The method according to claim 1, wherein the tip is filled with beads and wherein the liquid comprises different layers of fluids said fluids having one or more substance of interest, wherein by movement of the beads from a fluid to another fluid, mixing or a change of concentration of one or more substance are achieved within the tip.

4. The method according to claim 1, wherein, an external force is applied to a said bead cluster in order to keep said bead cluster inside the tip during the evacuation of the fluid from the tip itself.

5. The method according to claim 1, wherein once the magnetic beads are clustered, the liquid is evacuated at a controlled flow rate in order to avoid generation of fluid-dynamic turbulences whose shearing forces are bigger than cohesion forces of the bead cluster.

6. The method according to claim 5, wherein fluid dynamic turbulences are generated inside the tip in order to suspend the bead cluster after the bead cluster has fallen within the tip, without evacuating and evacuating the sample solution or filling the tip with new fluid.

7. The method according to claim 1, wherein the beads are moved by an action of the liquid hander and the external force, either simultaneously or sequentially that allows separation of the beads from the liquid, said external forces selected from the group consisting of: electromagnetic, acoustic, thermal, gravitational and magnetic.

8. The method according to claim 1, wherein the bead cluster is aspirated within the tip of the liquid handler such that the liquid handler allows washing, elution or dying of the beads.

9. The method according to claim 3, wherein an additional layer of fluids, oils, gels or solutions is added to the liquid in order to minimize diffusion among the layers.

10. The method according to claim 1, wherein a washing action is implemented directly inside the tip in order to remove any possible residual of unwanted substance in the bead cluster.

11. A method for separating beads, comprising:
    providing a liquid containing beads into a volume in a tip of a liquid handler, wherein at least some beads have magnetic properties;
    applying a magnetic field to at least a portion of the volume;
    varying the magnetic field applied onto the volume over time, whereas one or more magnetic field profiles provide an optimized gradient of the magnetic field along a vertical axis of said volume; and
    separating the magnetic beads from the liquid into a bead cluster by action of the optimized gradient of the magnetic field.

12. The method of claim 11, further comprising:
    performing a dynamic sweep of the volume with respect to the position of one or more magnets providing the one or more magnetic field profiles.

13. The method of claim 12, further comprising:
    designing a magnetic field profile of the one or more magnets to collect the beads present in the volume and move them in a region where the total magnetic field gradient has its maximum.

14. The method of claim 13, further comprising:
wherein the magnetic field profile of the one or more magnets exploits an inner well of the volume.

\* \* \* \* \*